(12) United States Patent
Wang et al.

(10) Patent No.: US 7,560,114 B2
(45) Date of Patent: Jul. 14, 2009

(54) **IMMUNO-MODULATING ANTITUMOR ACTIVITIES OF *GANODERMA LUCIDUM* (REISHI) POLYSACCHARIDES**

(76) Inventors: Yuan-Yuan Wang, 4F, No. 8, Chi-Yuan 1st Road, Sec. 1, Taipei (TW); Kay-Hooi Khoo, 3F, No. 16, Alley 12, Lane 118, Jen-Al Road, Sec. 3, Taipei 106 (TW); Shui-Tein Chen, No. 27, Lane 188, Wu-Long Street, Taipei 105 (TW); Chun-Cheng Lin, 28 Alley, 184 Nan-Yang Road, Feng-Yuan, Tai-Chun County, Taipei (TW); Chi-Huey Wong, P.O. Box 8154, Rancho Santa Fe, CA (US) 92067; Chun-Hung Lin, 7F, No. 102 Chao-Chow Street, Taipei (TW); Hong-Sen Chen, No. 289, Sec. 2, Chang-Shui Road, Shiou-Shui Village, Chang-Hua County (TW); Yow-Fu Tsai, No. 4, Lane 156, Nan-Ya Street, Hsin-Chu City (TW)

(*) Notice: Subject to any disclaimer, the term of this patent is extended or adjusted under 35 U.S.C. 154(b) by 0 days.

(21) Appl. No.: 11/952,032

(22) Filed: Dec. 6, 2007

(65) Prior Publication Data
US 2008/0267991 A1 Oct. 30, 2008

Related U.S. Application Data

(62) Division of application No. 11/553,402, filed on Oct. 26, 2006, now Pat. No. 7,323,176, which is a division of application No. 10/213,257, filed on Aug. 6, 2002, now Pat. No. 7,135,183.

(60) Provisional application No. 60/310,285, filed on Aug. 6, 2001.

(51) Int. Cl.
*A61K 36/06* (2006.01)
*A61K 9/00* (2006.01)

(52) U.S. Cl. .................... 424/195.15; 424/400
(58) Field of Classification Search ........................ None
See application file for complete search history.

(56) References Cited

U.S. PATENT DOCUMENTS

| 4,522,811 | A | 6/1985 | Eppstein |
|---|---|---|---|
| 5,334,704 | A | 8/1994 | Tsunoo et al. |
| 6,395,310 | B1 | 5/2002 | Iwasaki |
| 6,464,982 | B1 | 10/2002 | Lam |
| 6,471,860 | B1 | 10/2002 | Miltenyi |
| 6,613,754 | B1 | 9/2003 | Wu |
| 7,135,183 | B1 | 11/2006 | Wang et al. |
| 7,323,176 | B2 | 1/2008 | Wang et al. |
| 2003/0068329 | A1 | 4/2003 | Kosuna |
| 2003/0095981 | A1 | 5/2003 | Wong |
| 2007/0104729 | A1 | 5/2007 | Wang et al. |
| 2007/0105814 | A1 | 5/2007 | Hua et al. |
| 2007/0231339 | A1 | 10/2007 | Yu et al. |
| 2008/0214442 | A1 | 9/2008 | Yu et al. |
| 2008/0247989 | A1 | 10/2008 | Shih et al. |

FOREIGN PATENT DOCUMENTS

| WO | WO/2006/044616 | 4/2006 |
|---|---|---|
| WO | WO/2007/047021 | 4/2007 |
| WO | WO/2008/036421 | 3/2008 |

OTHER PUBLICATIONS

Blomberg K. et al., *Fluorescent europium chelates as target cell markers in the assessment of natural killer cell cytotoxicity*, J. Immunol. Methods, 1993, vol. 160, pp. 27-34.

Braciale T. et al., *Antigen presentation: structural themes and functional variations*, Immunology Today, 1991, vol. 12, No. 4, pp. 124-129.

Bronte V. et al., *IL-2 Enhances the Function of Recombinant Poxvirus-Based Vaccines in the Treatment of Established Pulmonary Metastases*, J. Immunol., 1995, vol. 154, pp. 5282-5292.

Chen H. et al., *Studies on the immuno-modulating and anti-tumor activities of Ganoderma lucidum (Reishi) polysaccharides*, Bioorg. Med. Chem., 2004, vol. 12, pp. 5595-5601.

Chen-Bettecken U. et al., *IgM RNA switch from membrane to secretory form is prevented by adding antireceptor antibody to bacterial lipopolysaccharide-stimulated murine primary B-cell cultures*, Proc. Natl. Acad. Sci., USA, 1985, vol. 82, pp. 7384-7388.

Chien C., *Polysaccharides of Ganoderma lucidum alter cell immunophenotypic expression and enhance $CD56^+$ NK-cell cytotoxicity in cord blood*, Bioorg. Med. Chem., 2004, vol. 12, pp. 5603-5609.

Feltkamp M. et al., *Cytotoxic T lymphocytes raised against a subdominant epitope offered as a synthetic peptide eradicate human papillomavirus type 16-induced tumors*, Eur. J. Immunol., 1995, vol. 25, pp. 2638-2642.

Grohmann U. et al., *$CD8^+$ cell activation to a major mastocytoma rejection antigen, P815AB: requirement for tumor helper peptides in priming for skin test reactivity to a P815AB-related peptide*, Eur. J. Immunol., 1995, vol. 25, pp. 2797-2802.

Hellman M. et al., *Separation of Isomeric Polyphenyls by Adsorption Chromatography*, 1990, Analytical Chemistry, pp. 1206-1210.

(Continued)

*Primary Examiner*—Christopher R Tate
*Assistant Examiner*—Randall Winston
(74) *Attorney, Agent, or Firm*—Mark H. Krietzman; Mark Bentley; Luce, Forward, Hamilton & Scripps, LLP

(57) ABSTRACT

The present invention provides methods of modulating an immune response in an organism by administering medicinally active extracts and fractions, and a method for preparing the same by extracting and fractioning constituents from the tissue of components of *Ganoderma lucidum*.

7 Claims, 10 Drawing Sheets

OTHER PUBLICATIONS

Henderson R. et al., *Human Tumor Antigens are Ready to Fly*, Advances in Immunology, 1996, vol. 62, pp. 217-256.

Chung et al., (Anti Neoplastic Components of Korean Basidomycetes, Korean Journal of Mycology (1980) vol. 8, No. 2, pp. 107-114.

Mizuno et al., Fractionation Chemical Modification and Antitumor Activity of Water-insoluble Polysaccharides of the Fruit-body of *Ganoderma-lucidum*, Nippon Nogeidagaku Kaishi, (1985) vol. 58, No. 11, pp. 1143-1152.

T. Mosman, "Rapid Colorimetric Assay for Cellular Growth and Survival: Application to Proliferation and Cytotoxicity Assays", Journal of Immunological Methods: 65 (1983) pp. 55-63.

Y. Sone, et al., "Structures and Antitumor Activities of the Polysaccharides Isolated from Fruiting Body and the Growing Culture of Mycelium of *Ganoderma lucidum*", Agric. Biol. Chem., 49 (9) (1985) pp. 2461-2653.

T. Usui, et al., "Isolation and Characterization of Antitumor Active β-D-Glucans from the Fruit Bodies of *Ganoderma applanatum*", Carbohydrate Research, 115 (1983) pp. 273-294.

T. Miyazaki, et al., "Structural Examination of an Alkali-Extracted, Water-Soluble Heteroglycan of the Fungus *Ganoderma lucidum*", Carbohydrate Research, 109 (1982), pp. 290-294.

B. L. Somani, et al., "A Modified Antrone-Sulfuric Acid Method for the Determination of Fructose in the Presence of Certain Proteins", Analytical Biochemistry, 167, (1987), pp. 327-330.

M. A. Jermyn, "Increasing the Sensitivity of the Anthrone Method for Carbohydrate", Analytical Biochemistry, 68, (1975), pp. 332-335.

M. N. Halhoul, et al., "Differential Determination of Glucose and Fructose, and Glucose- and Fructose- Yielding Substances with Anthrone", Analytical Biochemistry, 50, (1972), pp. 337-343.

R. Bowden, et al., "Alteration of Cytokine Levels in Murine Retrovirus Infection: Modulation by Combination Therapy", International Journal of Immunopharmacology 21 (1999), pp. 815-827.

E. Murphy, et al., "Detection of in vivo Expression of Interleukin-10 Using a Semi-Quantifative Polymerase Chain Reaction Method in Schistosoma Mansoni Infected Mice", Journal of Immunological Methods, 162, (1993), pp. 211-223.

D. H. Spackman, et al., "Automatic Recording Apparatus for Use in the Chromatography of Amino Acids", Analytical Chemistry, vol. 30, No. 7, (Jul. 1958), pp. 1190-1206.

C. H. Lo et al., Simple Fractionation of Phospholipase $A_2$ Analogues from Snake Venom by High-Performance Liquid Chromatography, Journal of Chromatography, 530, (1990), pp. 129-136.

G. Franz, "Polysaccharides in Pharmacy: Current Applications and Future Concepts", Planta Medica, 55, (1989), pp. 493-497.

E. Furusawa, et al., "Antitumor Activity of *Ganoderma lucidum*, an Edible Mushroom, on Intraperitoneally Implanted Lewis Lung Carcinoma in Synergenic Mice", Phytotherapy Research, vol. 6, (1992), pp. 300-304.

J. C. Sanchez, et al., The Mouse Swiss-2D Page database: A Tool for Proteomics Study of Diabetes and Obesity;, Proteomics, 1, (2001), pp. 136-163.

S. Y. Wang, et al., "The Anti-Tumor Effect of *Ganoderma lucidum* is Mediated by Cytokines Released from Activated Macrophages and T Lymphocytes", Int. J. Cancer. 70, (1997), pp. 699-705.

V. Větvička, et al., Soluble β-Glucan Polysaccharide Binding to the Lectin Site of Neutrophil or Natural Killer Cell Complement Mediating Cytotoxicity of iC3b-Opsonized Target Cells', The American Society.

J. A. G. Van Strijp, et al., Ligand Specificity of Purified Complement Receptor Type Three (CD11b/CD18, $\alpha_m\gamma_2$, Mac-1), The Journal of Immunology, vol. 151, No. 2, (Sep. 15, 1993), pp. 3324-3336.

Antje Müller, et al., "Receptor Binding and Internalization of a Water-Soluble (1→3-β-D-Glucan Biologic Response Modifier in Two Monocyte/Macrophage Cell Lines", The Journal of Immunology, 156, (1996), pp. 3418-3425.

Y. Y. Wang, et al., Studies on the Immuno-Modulating and Antitumor Activities of *Ganoderma lucidum* (Reishi) Polysaccharides: Functional and Proteomic Analyses of a Fucose-Containing Glycoprotein Fraction Responsible for the Activities:, Bioorganic & Medicinal Chemistry 10 (2002) pp. 1057-1062.

Courtesy International Search Report, PCT/US05/36961 dtd. Jun. 27, 2006.

Courtesy International Search Report, PCT/US06/37028, dtd. Mar. 22, 2007.

Gel A  Gel B

Gel C  Gel D

SEQUENCE LISTING

```
<160> NUMBER OF SEQ ID NOS: 23

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caaccaacaa gtgatattct ccatg                                           25

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gatccacact ctccagctgc a                                               21

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgatggacct acaggagctc ctgag                                           25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 4
gagtcaaatc cagaacatgc cgcag                                           25

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgaggtcac aggagaaggg acgccatgca                                      30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcattcatgg agcagcttat cgatgaatcc                                      30

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtgacaacca cggccttccc tact                                            24

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggtagctatg gtactcca                                                   18

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgttgtagag gtggactgg                                                  19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 10
tggcaggaca ctgaatactt                                                   20

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tggaggaact ggcaaaagga tggt                                              24

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttgggacaat ctcttcccca c                                                 21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcgacgtgga actggcagaa g                                                 21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggtacaaccc atcggctggc a                                                 21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgtggtctac agcctctcag cac                                               23

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 16 caaagggat atcagtcaga aaggt                                              25

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atccaggcca gcggctcgg                                                    19

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gggctttctg ctcaggtcta g                                                 21

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtagccacat gattgggaat gg                                                22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcatggaaag ttcggacaca gg                                                22

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acgacccctt cattgacc                                                     18

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
```

```
agacaccagt agactccacg                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tttttttttt tttttttttt                                              20
```

IMMUNO-MODULATING ANTITUMOR ACTIVITIES OF *GANODERMA LUCIDUM* (REISHI) POLYSACCHARIDES

RELATED APPLICATIONS

This application is a divisional of application Ser. No. 11/553,402, filed Oct. 26, 2006, now U.S. Pat. No. 7,323,176 which is a divisional of application Ser. No. 10/213,257, filed Aug. 6, 2002, now U.S. Pat. No. 7,135,183, issued Nov. 14, 2006, which claims the benefit of U.S. Provisional Application No. 60/310,285, filed Aug. 6, 2001, the disclosures of each of which are incorporated herein by reference in their entirety.

SEQUENCE LISTING

This application contains a sequence listing, submitted in both paper via EFS and a Computer Readable Form (CRF). The electronic file is identical to the computer readable copy of the Sequence Listing filed in U.S. Utility patent application Ser. No. 10/213,257, filed Aug. 6, 2002, which is incorporated by reference.

BACKGROUND

1. Field of the Invention

The present invention provides medicinally active extracts and fractions, and methods of preparing the same, from components of *Ganoderma lucidum*. These extracts and fractions have been found to be especially active in inhibiting tumor growth, modulating immune response, and increasing hematopoietic activity.

2. Description of the Related Art

*Ganoderma lucidum* (Reishi or Ling-Zhi) has been used in traditional Chinese medicine (TCM) as anti-tumor and immnuo-modulating agent. It also exhibits liver protective, hypoglycemic and platelet aggregation-inhibiting activities[1a], in addition to being effective in treating hypertension and neoplasia[1b]. The active constituents responsible for each of these activities have been qualitatively described, but the molecular basis of their action has not been elucidated. Of particular significance among these functions is its immnuo-modulating and anti-tumor activities.[2,3] Previous studies have shown that the polysaccharide components of Reishi exhibit the anti-tumor activity[2] and are able to stimulate the expression of CD4 and T-cell counts during or after chemotherapy. The saccharides contain either a polysaccharide backbone with β-1,3-linkages[3,4] or a polymannose backbone with β-1,4-linkages,[5a] both with side chains of unknown structure (Scheme 1). The real carbohydrate epitope responsible for the anti-tumor activity and its receptor has not been identified, though the receptor CR3 has been shown to bind the β-glucan polysaccharide with undefined side chains.[3b]

SUMMARY

The present invention provides a glycoprotein fraction which is shown to stimulate spleen-cell proliferation and expression of such cytokines as interleukins I and II, and interferon γ. Proteomic analysis of mouse spleen cells treated with this glycoprotein showed ~50% change in the proteome. The composition of this glycoprotein has been determined, and the saccharide moiety has been confirmed to be responsible for the activities. Furthermore, the presence of fucose in the saccharide is required for the activities.

One particular glycoprotein fraction of the present invention was found to enhance the production of GM-CSF and INF-γ 20-fold higher than the treatment with crude Reishi extract.

The carbohydrate composition analyses of crude Reishi extract indicated that glucose and mannose exist as the major components together with smaller amounts of other sugars, including fucose, N-acetylglucosamine, xylose and rhamnose (Table 1). The crude extract contains 15.6% proteins, the amino acid analysis of which was shown in Table 2.

The crude extract of Reishi is currently available as a traditional Chinese medicine. To identify the active component, gel filtration chromatography of the crude Reishi extract was carried out by using a Sephacryl S-500 column eluted with 0.1 N Tris buffer (pH 7.0), and the sugar content of each fraction was determined by anthrone analysis or phenol-sulfuric acid method[5b]. Five fractions were obtained and the main fraction was designated as fraction 3 (FIG. 1). The colorimetric assay using 3-(4,5-dimethylthiazol-2-yl)-2,5-diphenyl tetrazolium bromide (MTT) for cell proliferation was then carried out to evaluate Con A-stimulated mouse spleen cells in the presence of various concentrations of the crude Reishi extract and fractions 1-5. In comparison with the control experiment (without treatment of samples), the cell proliferation activity was significantly enhanced with fraction 3 and slightly enhanced with fraction 2. The optimal concentration of fraction 3 was between 0.01 and 0.1 μg/mL and that of crude Reishi extract was between 0.1 and 1.0 μg/mL, as shown in FIG. 2. Carbohydrate analysis of fraction 3 was further carried out, and it was found that the relative composition is similar to that of the crude extract (Table 3), except that the galactose content increases.

RT-PCR experiments were next used to identify the cytokines expressed in mouse spleen cells after treatment with fraction 3 and the crude extract. In the presence of 10 μg/mL of fraction 3, IL-1, IL-2 and INF-γ were observed to express significantly (FIG. 3). At a concentration range of 0.1 to 100 ppm of fraction 3, among ten cytokines tested—IL-1, IL-2, IL-4, IL-6, IL-12, INF-γ, TNF-α, GM-CSF, G-CSF and M-CSF, most of them were up-regulated significantly except for IL-2 and IL-4 (FIG. 5), when compared with the negative (no treatment) and positive (treated with Con A) controls. The results implied that fraction 3 was able to stimulate the inflammatory response due to the expression of IL-1, IL-6 and TNF-α. The expression of INF-γ and TNF-α was suggested for the anti-tumor activity, and that of GM-CSF, G-CSF and M-CSF was possibly associated with hematopoiesis.

Since IL-12, instead of IL-4, was expressed in the splenocyte incubation with fraction 3, the development of the $T_H1$ subset was likely involved in the cell-mediated response. Based on the consideration that INF-γ up-regulates IL-12 production and activates the IL-12 receptor on activated T cells, $T_H1$ development was also dependent on INF-γ. Moreover, although crude Reishi extract and fraction 3 both induced a similar pattern of cytokine expression at the same dosage (0.1-100 μg/mL), the latter showed the expression at much higher level, especially in the expression of IL-1β, IL-6, INF-γ, TNF-α, GM-CSF, and G-CSF. The outcome also supported the conclusion that the major activity of crude Reishi extract is concentrated in fraction 3.

Moreover, treatment of mouse spleen cells with fraction 3 (10 μg/mL) resulted in a significant change of the proteome. FIG. 4a (no treatment, control) and FIG. 4b (treatment with fraction 3) show 623 and 568 detectable spots in the 2-D electrophoresis, respectively. Further analysis indicated that ~191 spots disappear after the treatment (FIG. 4c) and 137 spots appear after the treatment (FIG. 4d). The data-imaging comparison demonstrated that there is ~50% change in the proteome. Overall, there are 431 spots matched before and after treatment, and 137 spots (24.1%) not matched.

On the basis of colorimetric sandwich ELISA, the quantitative measurement for the expressed cytokines revealed an intriguing feature. As shown in FIG. 7, the individual treatment of mouse splenocytes with crude Reishi extract, fraction 3 and F3 G2 led to the GM-CSF production at the concentration of 0.91, 10.4 and 24.0 pg/mL, respectively, after the incubation for 72 h. Similar enhancement was obtained when the ELISA assay was carried out for the INF-γ expression (FIG. 8). The treatment with F3G2 and fraction 3 were able to stimulate the spleen cells to generate 143 and 8.6 pg/mL INF-γ, respectively, after the 48-h incubation.

The carbohydrate composition analyses of crude Reishi extract, fraction 3, F3G1, F3G2 and F3G3 all indicated that glucose and mannose exist as the major components together with smaller components of other sugars including fucose, galactose, N acetylglucosamine and xylose (Table 3). It is of interest that the percentage of galactose decreased significantly in F3G2 and F3G3. Work is in progress to determine the correlation among the composition, structure and activity in these partially purified fractions of Reishi extract.

To further understand the composition and activity of fraction 3, it was treated with protease K to partially destroy the protein component. The result showed that proliferation of Con A-stimulated spleen cells remained the same. Glycolytic cleavage by α1,2-fucosidase, however, abolished the activity of fraction 3 completely (based on MTT assay). In contrast, the activity of fraction 3 was slightly reduced after treatment with α1,3/4-fucosidase. This experiment establishes that the active component is a polysaccharide or glycopeptide containing terminal fucose residues with α1,2-fucosidic linkages. Overall, as shown in Scheme 2, the main active component is a glycoprotein containing essential terminal fucose residues with α1,2-linkages. The protein moiety is not required for the activity. Work is in progress to determine the minimal epitope of the fuco-saccharide and to identify the receptor for structure-activity relationship study.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings:

FIG. 2A is an assay of the crude Reishi extract, and FIG. 2B is an assay of fraction 3.

In FIG. 4A, Gel A shows cells with no treatment and Gel B shows cells treated with fraction 3. In FIG. 4B, Gel C shows disappearing spots when Gel A is compared with Gel B, and Gel D shows the appearing spots when Gel A is compared with Gel B.

DETAILED DESCRIPTION

EXAMPLE 1

Figure 1:
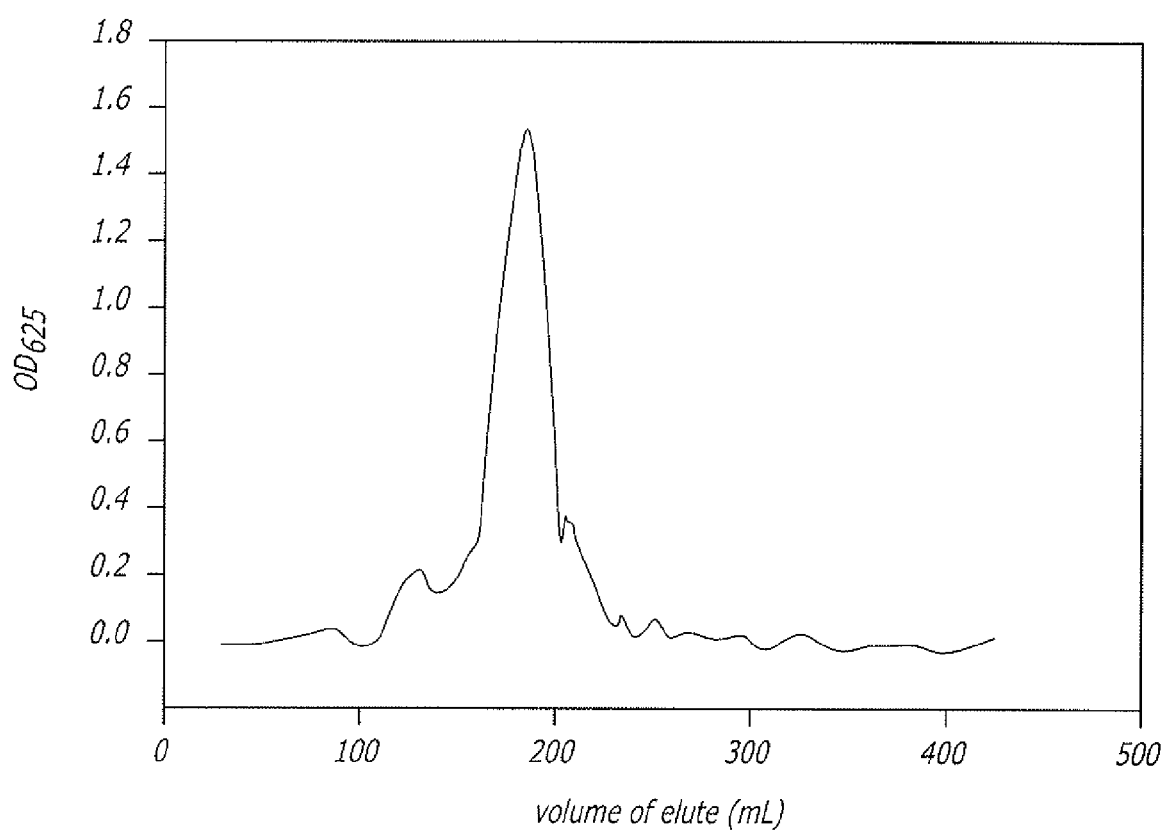
FIG. 1 depicts the fractionation of Reishi extract by gel filtration chromatography using a Sephacryl S-500 column (fraction 1: 100 to 130 mL; fraction 2: 130 to 155 mL; fraction 3: 155 to 205 mL; fraction 4: 205 to 220 mL; fraction 5: 220 to 255 mL).
Figure 2A:
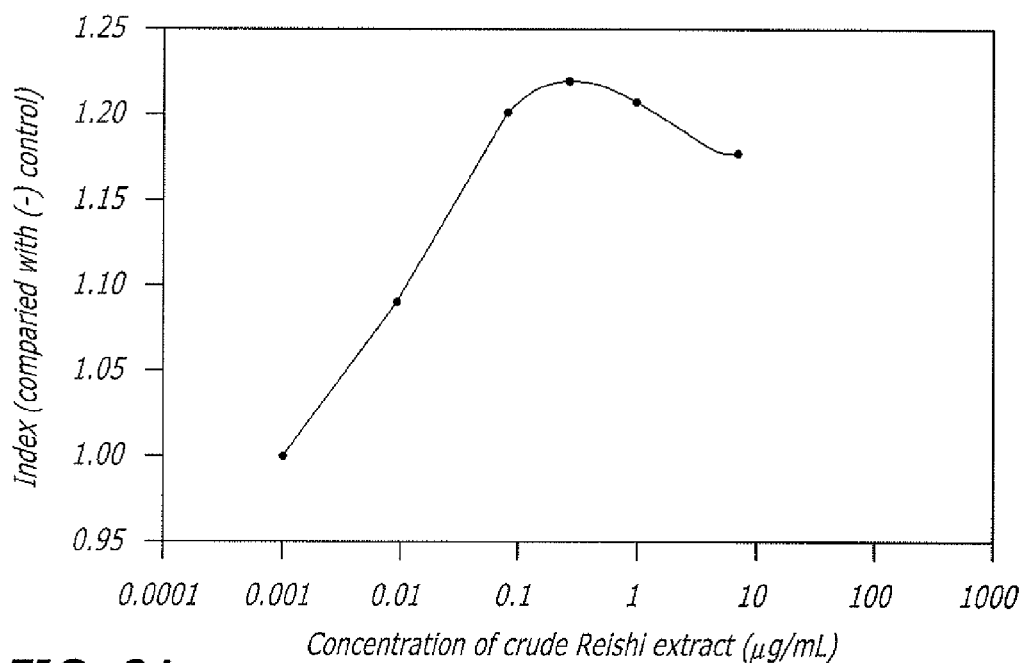
FIGS. 2A-2B depicts the colorimetric assay (MTT) for Con A-stimulated cell proliferation.
Figure 2B:
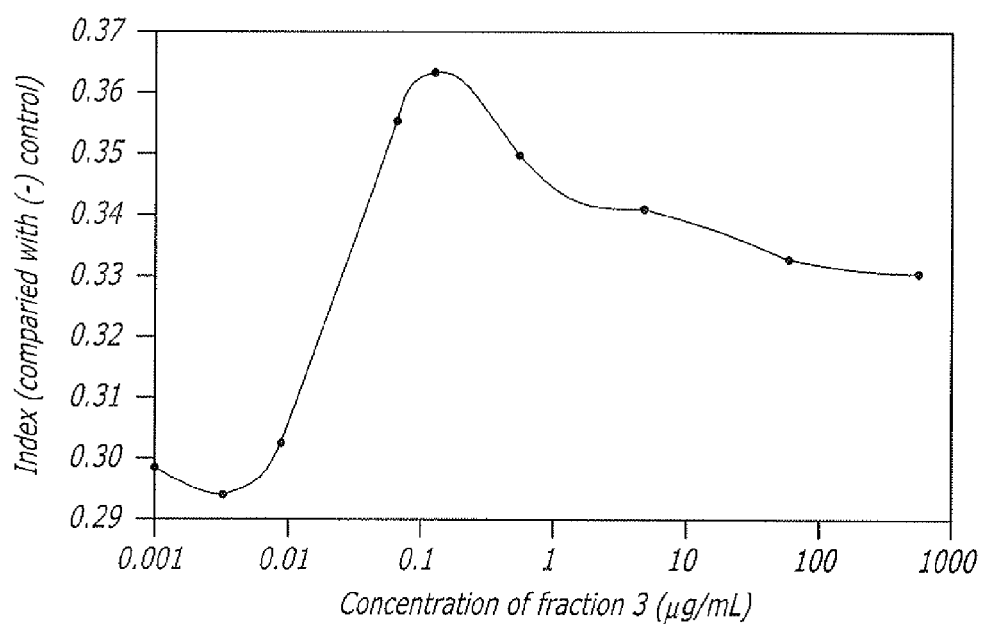
Figure 3A:
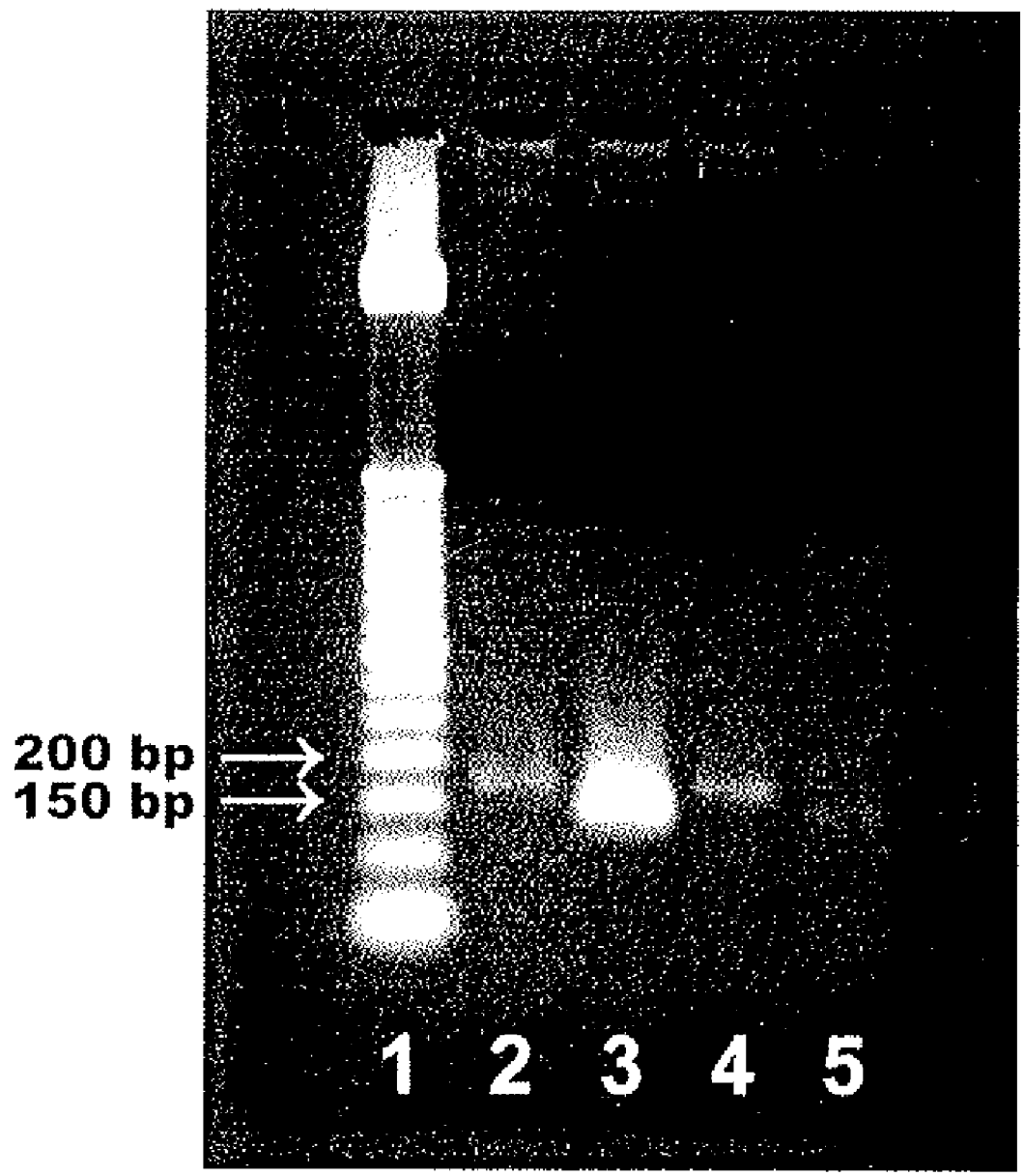
FIG. 3A-FIG. 3C depicts the results of the gel electrophoresis of the RT-PCR experiments to detect the expression of IL-1 (FIG. 3A), IL-2 (FIG. 3B), IFN-γ (FIG. 3C) when spleen cells are incubated with fraction 3. Column 1 shows the molecular weight marker (50 bp ladder); column 2 shows the house keeping gene (200 bp) in the presence of fraction 3; column 3 shows IL-1 expression (152 bp) in the presence of fraction 3 (FIG. 3A), IL-2 expression (167 bp) in the presence of fraction 3 (FIG. 3B) or IFN-γ expression (336 bp) in the presence of fraction 3 (FIG. 3C); column 4 shows the house keeping gene in the absence of fraction 3; and column 5 shows no obvious IL-1 expression in the absence of fraction 3.
Figure 3B:
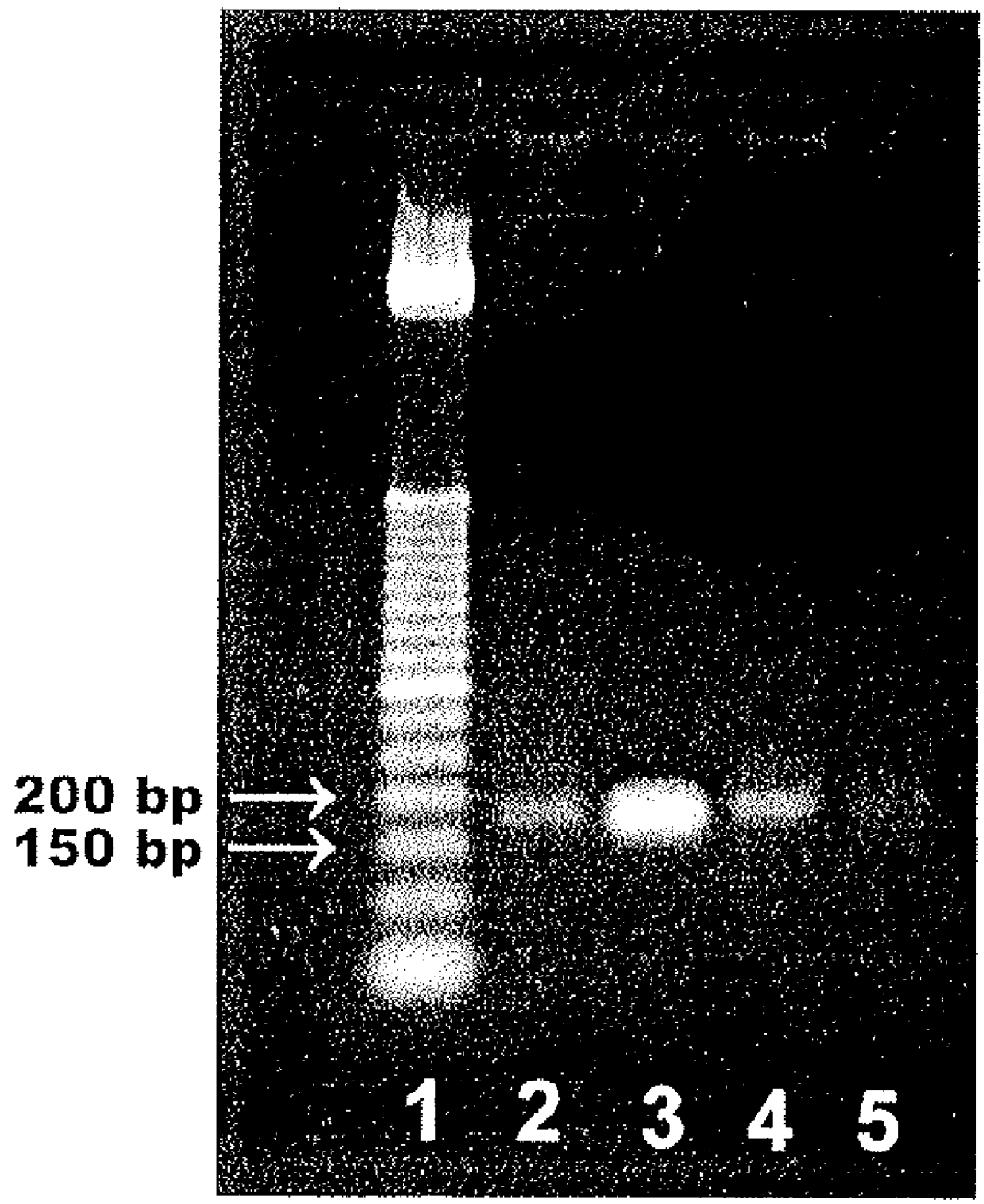
Figure 3C:
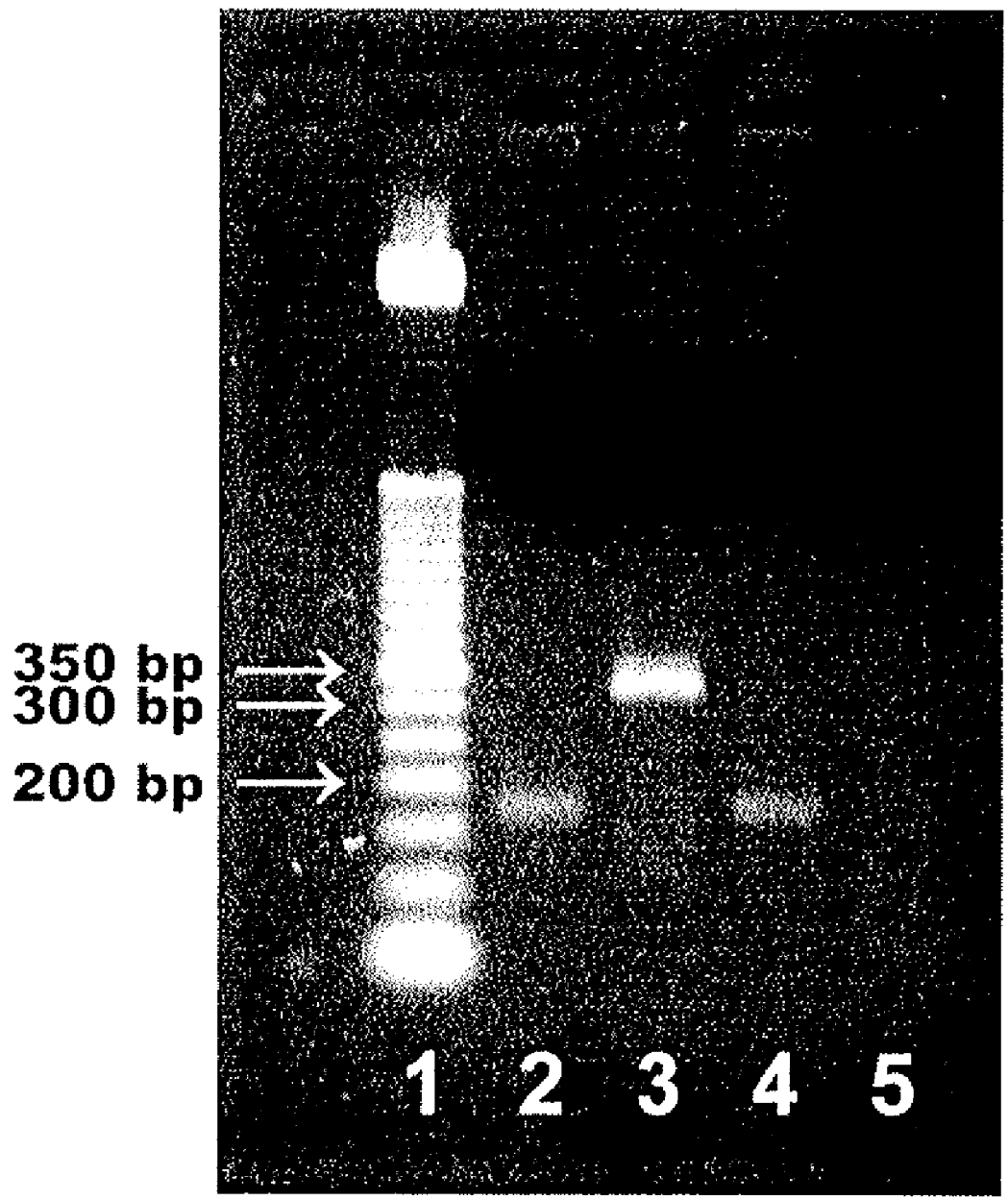
Figure 4A:
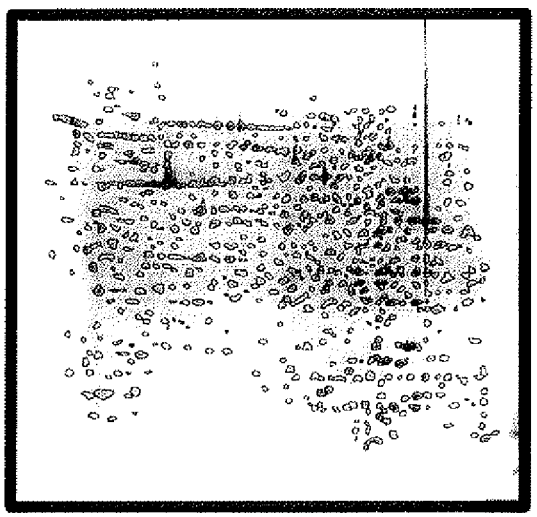
FIGS. 4A-4B shows the proteomic analysis of the mouse spleen cells treated with fraction 3.
Figure 4A:
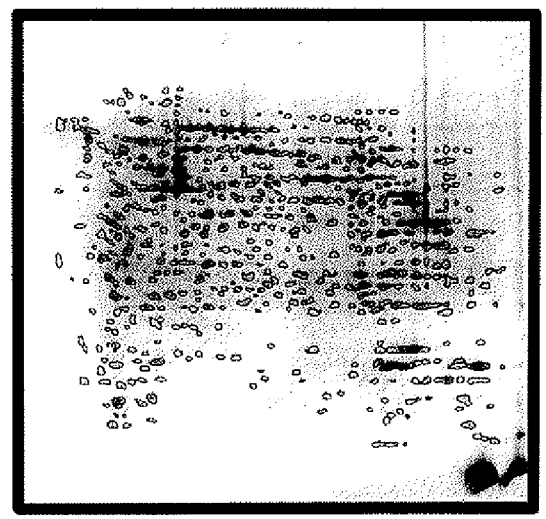
Figure 4B:
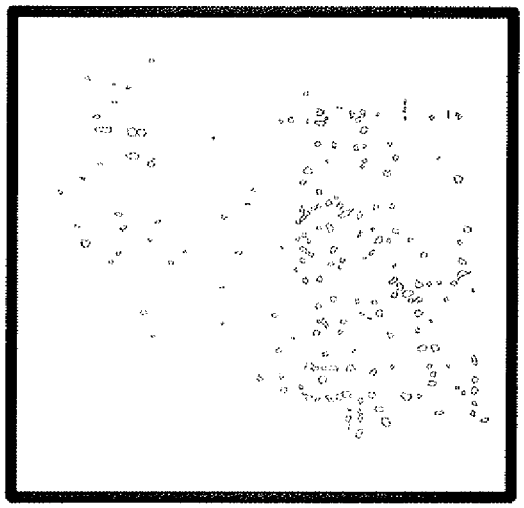
Figure 4B:
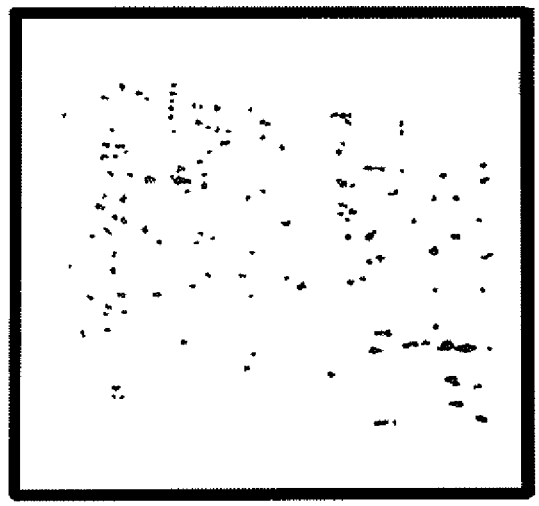
Figure 5:
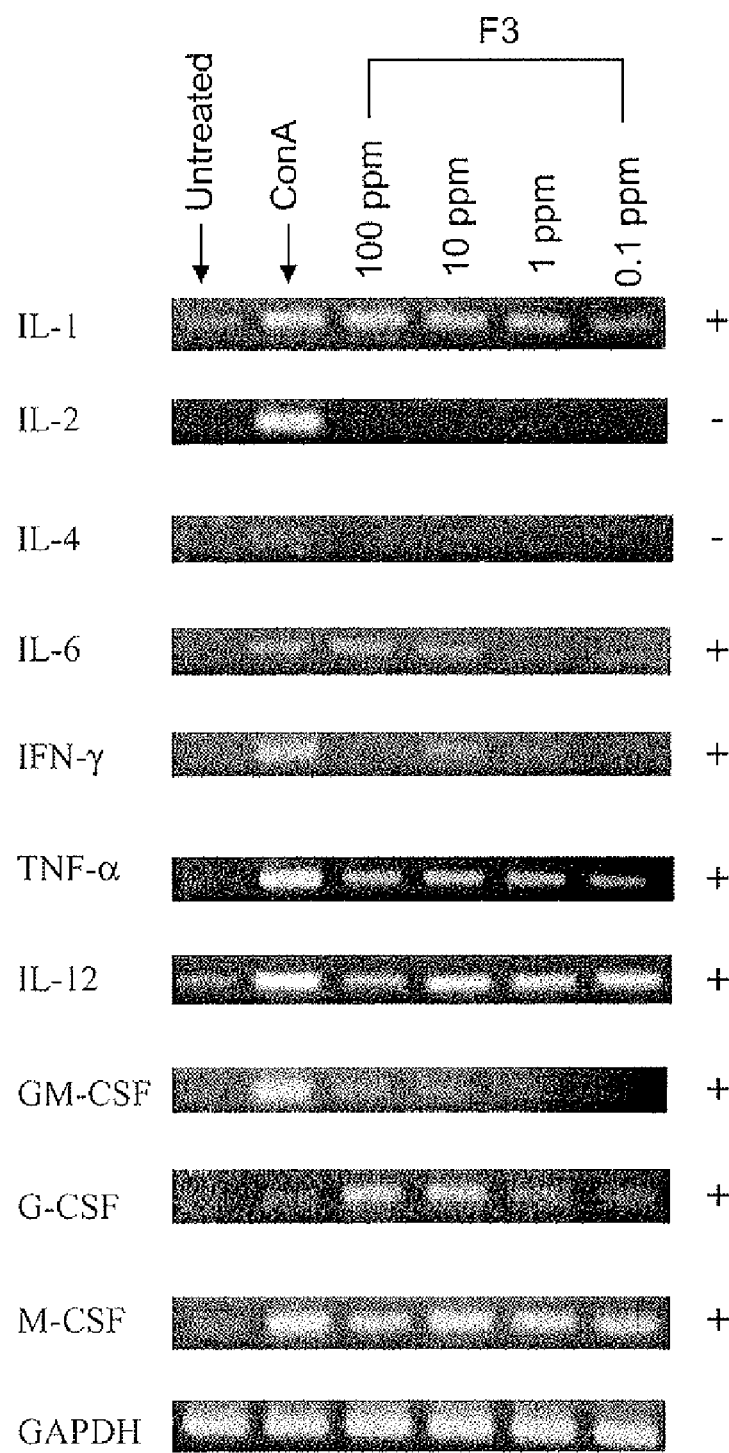
FIG. 5 depicts the results of the gel electrophoresis of the RT-PCR experiments to detect the expression often different cytokines when mouse spleen cells are incubated with or without fraction 3 at the concentration of 0.1, 1, 10, 100 ppm for 6 hours.

Materials. Crude Reishi extract (prepared via alkaline extraction (0.1 N NaOH), neutralization and ethanol precipitation) was obtained from Pharmanex Co. (CA, USA). Immobiline DryStrip (pH 3-10 NL (non-linear), 18 cm) and IPG buffer (pH 3-10 NL) were purchased from Amersham Pharmacia Biotech (Uppsala, Sweden). CHAPS, Tris buffer, agarose, iodoacetamide and alpha-cyano-4-hydroxycinnamic acid were from Sigma Co. (St. Louis, Mo., USA); dithioerythreitol (DTE) was from Merck Co. (Darmstast, Germany); acrylamide, ammonium persulfate (APS) and TEMED were from Bio-Rad (Hercules, Calif., USA); sodium dodecyl sulfate (SDS) and glycine were from Fluka (Buchs, Switzerland); sequencing grade trypsin was from Promega (Madison, Wis., USA).

Purification of Reishi extract. Twenty eight mg of the crude extract were dissolved in 2 mL of Tris buffer (pH 7.0, 0.1 N) and centrifuged to remove the insoluble materials (7 mg). The supernatant was purified by gel filtration chromatography using a Sephacryl S-500 column (100 cm×1.6 cm) with 0.1 N Tris buffer (pH 7.0) as the eluent. The flow rate was set at 0.5 mL/min, and 7.5 mL per tube was collected. After the chromatography, each fraction was subjected to anthrone analysis to detect sugar components. Five fractions were collected (fractions 1-5), each dialyzed to remove excessive salt and lyophilized to give 1.0, 6.2, 5.3, 2.1, and less than 1 mg, respectively.

Anthrone colorimetric method.[6] Each 1.5 mL of anthrone (9,10-dihydro-9-oxoanthracene) solution (0.2 g anthrone dissolved in 100 mL of conc. sulfuric acid) in a series of test tubes immersed in an ice water bath was carefully overlayed with 1.5 mL of sample (20-40 μg/mL of D-glucose or equivalent). After all additions had been made, the tubes were shaken rapidly and then replaced in an ice water bath. The tubes were heated for 5 min in a boiling water bath and then cooled; the optical densities were read within an hour at 625 nm against distilled water. Standards, reagent blanks and unknowns were run in triplicate because of likely contamination by other carbohydrate sources. Calculations were made on the basis that the optical densities are directly proportional to the carbohydrate concentration.

Mitogen-induced proliferation of spleen cells and colorimetric MTT assay.[7] Whole spleen cells were harvested from BALB/c male mice (six weeks old), suspended in RPMI-1640 medium containing 10% FCS (fetal calf serum), and centrifuged to remove the supernatant. The collected precipitated cells were first suspended in 1 mL of RBC lysis buffer (8% $NH_4Cl$), then 14 mL more of the same lysis buffer were added to destroy red blood cells. After 1 min, the solution was diluted with 15 mL RPMI-1640 medium to stop the reaction, centrifuged to collect the cells, and adjusted the cell final concentration to $2\times10^6$ cells/mL with RPMI-1640 medium. Concanavalin A (Con A, final conc: 1 μg/mL) was added to the resulting mixture. The cells were incubated with or without a Reishi extract (or partially purified fraction) in 96-well ELISA plates at 37° C. with 5% $CO_2$ for 72 h. The cell proliferation was measured based on the MTT assay.

MTT (3-(4,5-dimethylthiazol-2-yl)-2,5-diphenyl tetrazolium bromide) was dissolved in phosphate buffered saline (PBS) at 5 mg/mL and filtered to sterilize and remove a small amount of insoluble residue present in some batches of MTT. At the times indicated below, 25 μL of MTT solution was added to all wells of an assay, and plates were incubated at 37° C. for 4 h. Acid-isopropanol (100 μL of 0.04 N HCl in isopropanol) was added to all wells and mixed thoroughly to dissolve the dark blue crystals. After a few minutes at room temperature to ensure that all crystals were dissolved, the plates were read on a Perkin Elmer ELISA reader (HTS 7000 plus), using a test wavelength of 570 nm, a reference wavelength of 620 nm. Plates were normally read within 1 h after the addition of isopropanol.

Reverse transcription (RT) and polymerase chain reaction (PCR).[8] Mouse spleen cells were aseptically removed from healthy mice (BALB/c male mice, six weeks old), adjusted to an ideal cell concentration ($4\times10^6$ cells/mL) and incubated in RPMI-1640 medium containing 10% of FCS (fetal calf serum) at 37° C. with 5% $CO_2$. After 6 h, the cells were subjected to RNA extraction using Qiagen RNAeasy mini kit to obtain ~1 μg of the desired RNA. Reverse transcription (RT) was performed using the Thermoscript R/T PCR System, and the Thermoscript system protocol I, from Gibco BRL. The reaction was carried out as follows: 8 μL of RNA, 2 μL of primer (Oligo(dT)$_{20}$) (SEQ ID NO:23), 2 μL of 10 mM dNTP Mix, and DEPC $H_2O$ (0.1% diethylpyrocarbonate-treated $H_2O$) was added to each tube, which was then incubated at 65° C. for 5 min and immediately put on ice. The following was added to each tube as a 8 μL mixture: 4 μL of 5×cDNA buffer, 1 μL of 0.1 M dithiothreitol (DTT), 1 μL of RNaseOut (a ribonuclease inhibitor) and 1 μL of Thermoscript R/T, and I μL of DEPC water. The mixture was incubated at room temperature for 10 min and then 55° C. for 30 min to allow first strand of cDNA synthesis. Enzyme activity was terminated by incubating the reactions at 85° C. for 5 min and the tubes were then placed on ice for 10 min. The samples were stored at −20° C. until used for PCR.

Each sample (3 μL) was added to each reaction tube and the following reagents were added as a 47 μL mix: 5 μL of 10×PCR buffer, 4 μL of 10 mM dNTP Mix, 2 μL of each primer (10 OD/mL, sense and anti-sense), 33 μL of DEPC $H_2O$, and 1 μL of ProZyme® (DNA polymerase, from PROtech Technology). The reaction tubes were placed in a Strategene PCR Robocycler (Gradient 96) and ran under the following condition: 1 cycle at 92° C. for 2 min (initial denaturation), then 30 consecutive cycles of 91° C. for 10 s (denaturation), 59° C. for 25 s (primer annealing) and 72° C. for 25 s (primer extension). The reactions were analyzed by gel electrophoresis.

Sugar composition analysis—TMS method. For monosaccharide analysis, the polysaccharide extracts/fractions were methanolyzed with 0.5 M methanolic-HCl (Supelco) at 80° C. for 16 h, re-N-acetylated with 500 μL of methanol, 10 μL of pyridine and 50 μL of acetic anhydride, and then treated with the Sylon HTP® trimethylsilylating reagent (Supelco) for 20 min at room temperature, dried and redissolved in hexane. GC-MS analysis of the trimethylsilylated derivatives was carried out using a Hewlett-Packard (HP) Gas Chromatograph 6890 connected to a HP 5973 Mass Selective Detector. Samples were dissolved in hexane prior to splitless injection into a HP-5MS fused silica capillary column (30 m×0.25 mm I.D., HP). The column head pressure was maintained at around 8.2 psi to give a constant flow rate of 1 mL/min using helium as carrier gas. Initial oven temperature was held at 60° C. for 1 min, increased to 140° C. at 25° C./min, to 250° C. at 5° C./min, and then increased to 300° C. at 10° C./min.

Amino acid composition analysis. The analysis was carried out based on a well-established method.[9] A sample of crude Reishi extract (6 mg) was dissolved in 1 mL solution of 6 M HCl and TFA (4/1), and heated at 140° C. for 3 h. The mixture was concentrated to give a dry residue and dissolved in 100 μL citrate buffer. A small aliquot (4 μL) was withdrawn and subjected to composition analysis by amino acid analyzer (Jeol JLC-6AH).

Sample preparation for proteomic studies. Reishi extract-treated mouse spleen cells were lysed in 350 μL of lysis buffer containing 8 M Urea, 2% CHAPS, 65 mM DTE, 2% v/v isocratic pH gradient (IPG) buffer pH 3-10 NL (non-linear), and a trace of bromophenol blue. The sample was centrifuged for 10 min at 13,000 rpm. The total protein concentration in the sample was measured using Bio-Rad protein concentration assay kit. Samples equal to 500 μg of proteins were loaded on immobilized pH gradient strips (pH 3-10 NL, 18 cm) for 2-dimensional electrophoresis.

2-Dimensional electrophoresis and image processing. The separations were performed as described by Hochstrasser et al.[10] The isoelectric focusing was carried out in an IPGPhor apparatus (Amersham Pharmacia Biotech). The second dimension was done in 10-15% polyacrylamide gradient gels using the Protean II xL 2D multi cell (Bio-Rad). Protein spots were stained with fluorescence dye Sypro Ruby™ (Molecular Probes).

Sypro Ruby-stained gels were scanned with fluorescence laser scanner (Bio-Rad) generating 10 Mb image. The images were analyzed with ImageMaster™ software (Amersham Pharmacia Biotech). For each gel the spots were detected and quantified automatically, using default spot detection parameters. Manual spot editing was performed in agreement with the visual inspection of the gels. The relative volume was calculated in order to correct any differences in protein loading and gel staining.

MALDI-TOF MS analysis. Sypro Ruby-stained protein spots were cut from the gel and washed with 200 μL of 50 mM ammonium bicarbonate, pH 8.5, buffer in 50% $CH_3CN$. Following dehydration in $CH_3CN$ and speed vacuum centrifugation, the gel pieces were swollen in a digestion buffer containing 100 mM ammonium bicarbonate, pH 8.5, 1 mM $CaCl_2$, 10% $CH_3CN$ and 50 ng of sequencing grade trypsin. The resulting peptides were extracted with 50% $CH_3CN$/5% TFA after overnight digestion. A 1 μL aliquot of peptide mixture was deposited on the MALDI target 96-well plate and after few seconds 1 μL of a matrix solution (α-cyano-4-hydroxycinnamic acid in 50% $CH_3CN$/0.1% TFA) was added. The mixture was allowed to dry at ambient temperature. Positive-ion mass spectrum was measured on a MALDI reflection time-of-flight mass spectrometer M@LDI (Micromass UK, Manchester, UK) equipped with a nitrogen laser. The reported spectra were accumulated from 50 to 100 laser shots.

General procedure of fucosidase treatment. A sample of ten mg of Reishi extract or fraction 3 in 50 mM citrate buffer (pH 6.0) was treated with α1,2- or α1,3/4-fucosidase (5 Unit) at 37° C. for a period of time (2-12 h). The mixture was heated in boiling water for 5 min to destroy the enzyme activity, dialyzed against $H_2O$ at 4° C., and lyophilized to give a dry powder for activity studies.

EXAMPLE 2

Materials. Crude Reishi extract (prepared via alkaline extraction (0.1 N NaOH), neutralization and ethanol precipitation) was obtained from Pharmanex Co. (CA, USA). All the chemicals and reagents were from Sigma Co. (81. Louis, Mo., USA) unless indicated.

Purification of Reishi extract. One hundred grams of crude Reishi extract were dissolved in 3 L of double distilled water, stirred at 4° C. for 24 h, and centrifuged for 1 h to remove the insoluble. The resulting solution was concentrated at 35° C. to give a small volume and lyophilized to generate 70 g powder of dark-brown color, 2.5 g of which were dissolved in a small volume of Tris buffer (pH 7.0, 0.1 N) and purified by gel filtration chromatography using a Sephacryl S-500 column (95 cm×2.6 cm) with 0.1 N Tris buffer (pH 7.0) as the eluent. The flow rate was set at 0.6 mL/min, and 7.5 mL per tube was collected. After the chromatography, each fraction was subjected to anthrone analysis or the phenol-sulfuric acid method to detect sugar components.

Five fractions were collected (fractions 1-5), each dialyzed to remove excessive salt and lyophilized to give 450 mg of fraction 3.

Fraction 3 was further subjected to a column of Diaion-W A30 anion exchanger (Cl-form, 40 cm×3.5 cm) eluted with 0.2 and 0.8 M NaCl at a flow rate of 0.5 mL/min and two fractions were designated as F3G1 (11% yield based on fraction 3) and F3G2 (10% yield based on fraction 3), respectively. Another fraction (F3G3, 11% yield based on fraction 3) was generated when the column was further eluted with 2 M NaOH.

The gel-filtration chromatography of F3G2 was carried out on a TSK HW-75 column (130 cm×2.6 cm) eluted with double distilled water at a flow rate of 0.5 mL/min. There were two fractions collected; i.e., G2H1 (19% yield based on F3G2) and G2H2 (69% yield based on F3G2).

Anthrone colorimetric method.[8] Each 1.5 mL of anthrone (9,10-dihydro-9-oxoanthracene) solution (0.2 g anthrone dissolved in 100 mL of conc. sulfuric acid) in a series of test tubes immersed in an ice water bath was carefully overlayed with 1.5 mL of sample (20-40 μg/mL of D-glucose or equivalent). After all additions had been made, the tubes were shaken rapidly and then replaced in an ice water bath. The tubes were heated for 5 min in a boiling water bath and then cooled; the optical densities were read within an hour at 625 nm against distilled water. Standards, reagent blanks and unknowns were run in triplicate because of likely contamination by other carbohydrate sources. Calculations were made on the basis that the optical densities are directly proportional to the carbohydrate concentration.

Reverse transcription (RT) and polymerase chain reaction (PCR).[9] Mouse spleen cells were aseptically removed from healthy mice (BALB/c male mice, six weeks old), adjusted to an ideal cell concentration ($3 \times 10^6$ cells/mL) and incubated in RPMI-1640 medium containing 10% of FCS (fetal calf serum) at 37° C. with 5% CO2. After 6 h, the cells were subjected to RNA extraction using Qiagen RNAeasy mini kit to obtain ~1 μg of the desired RNA. Reverse transcription (RT) was performed using the Thermoscript R/T PCR System, and the Thermoscript system protocol I, from Gibco BRL. The reaction was carried out as follows: 1 μg of RNA, 1 μL of primer (Oligo(dT)20) (SEQ ID NO:23) and 2 μL of 10 mM dNTP Mix were added to each 0.2 mL tube and adjusted the total volume to 12 μL with DEPC $H_2O$ (0.1% diethylpyrocarbonate-treated $H_2O$). The mixture was incubated at 65° C. for 5 min and immediately chilled on ice. The following was added to each tube as an 8 μL mixture: 4 μL of 5×cDNA buffer, 1 μL of 0.1 M dithiothreitol (DTT), 1 μL of RNaseOut (a ribonuclease inhibitor) and 1 μL of Thermoscript R/T, and 1 μL of DEPC water. The mixture was incubated at room temperature for 10 min and then 50° C. for 1 h to allow first strand of cDNA synthesis. Enzyme activity was terminated by incubating the reactions at 85° C. for 5 min and the tubes were then placed on ice for 10 min. The samples were stored at −20° C. until used for PCR.

Each sample (2 μL) was added to each reaction tube and the following reagents were added as a 25 μL mix: 2.5 μL of 10×PCR buffer, 2 μL of 10 mM dNTP Mix, 2.5 μL of 10 mM each primer (sense and anti-sense), 13 μL of DEPC $H_2O$, and 1 μL of ProZyme® (DNA polymerase, from PROtech Technology). The reaction tubes were placed in a Strategene PCR Robocycler (Gradient 96) and run under the following condition: 1 cycle at 94° C. for 2 min (initial denaturation), then 25 consecutive cycles of 94° C. for 1 min (denaturation), primer annealing (various temperatures depending on primers, see Table 5 for details) for 1 min and 72° C. for 1 min (primer extension). The reactions were analyzed by gel electrophoresis.

According to the RT-PCR studies for the cytokine expression (Table 4), the treatment with F3G2 led to significant expression of all the ten cytokines aforementioned, which was thus concluded to contain the major active components of fraction 3. The expression of TNF-α and IL-1 were detectable in the studies of F3G1 and F3G3. It is of interest that both fractions can trigger only the inflammatory pathway, unlike fraction 3 or F3G2.

Figure 6:
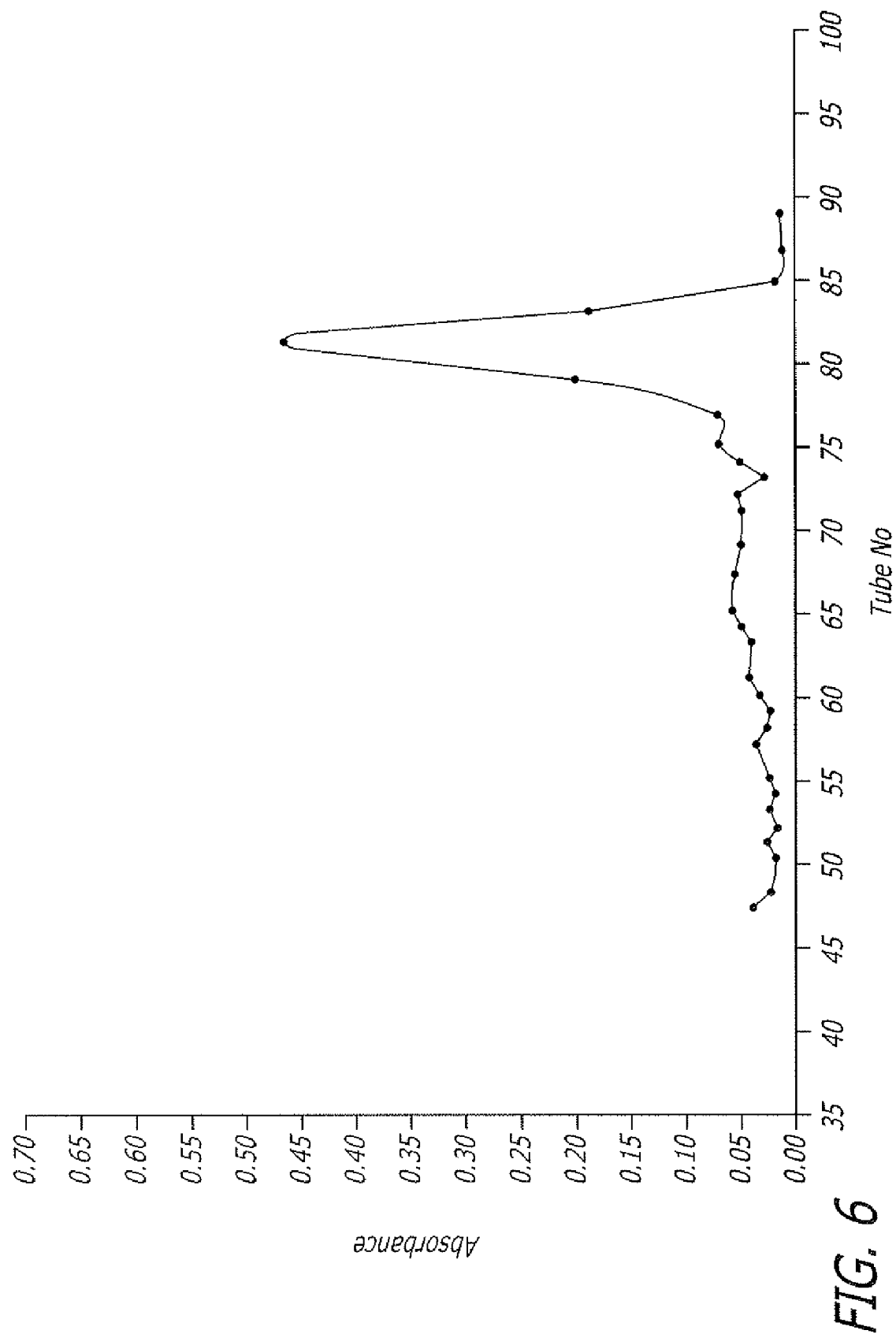
FIG. 6 depicts the chromatographic diagram to obtain fractions G2H1 and G2H2 from fraction F3G2.
Figure 7:
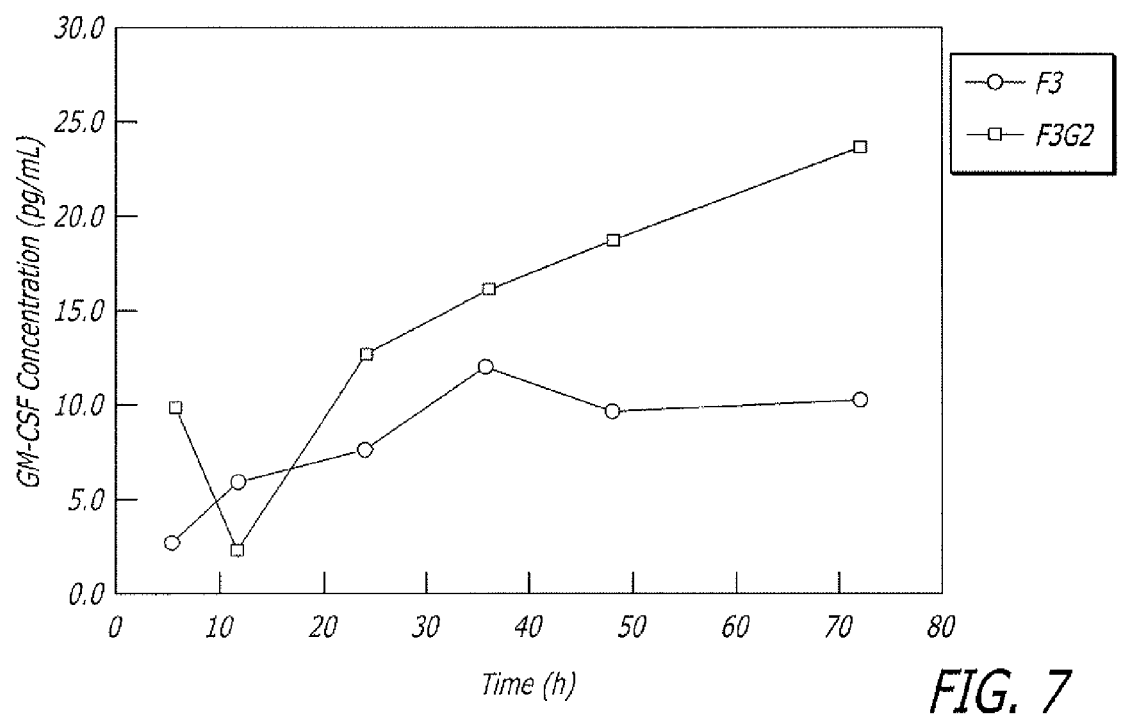
FIG. 7 depicts the GM-CSF expression by mouse splenocytes ($2.2 \times 10^6$ cells/mL) when the cells were treated with F3 (100 μg/mL) or F3G2 (100 μg/mL).
Figure 8:
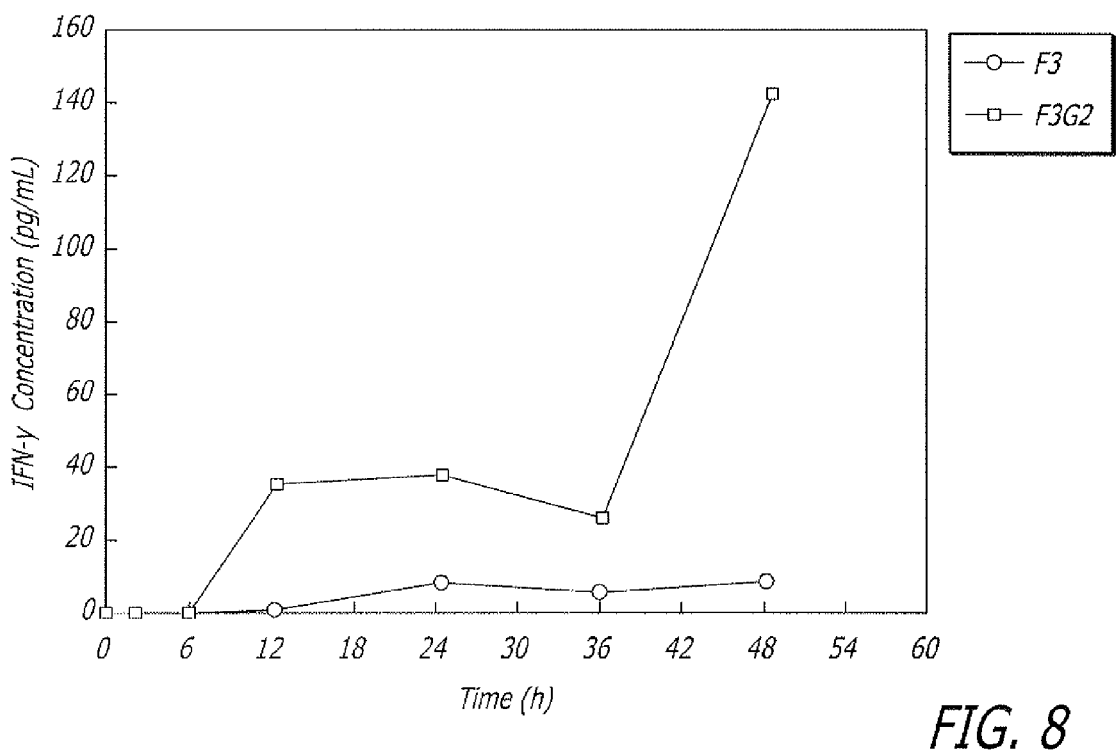
FIG. 8 depicts the INF-γ expression by mouse splenocytes ($3 \times 10^6$ cells/mL) when the cells were treated with F3 (100 μg/mL) or F3G2 (100 μg/mL).

The additional gel-filtration chromatography of F3G2 on a TSK HW-75 column resulted in two fractions—G2H1 (19% yield based on F3G2) and G2H2 (69% yield based on F3 G2), as shown in FIG. 6. The preliminary result from the RT-PCR studies revealed that the former fraction contains much higher activity than the same dosage of F3G2 and G2H2 in the expression of IL-1β, IL-6, INF-γ, TNF-α, and GM-CSF.

Sugar composition analysis—TMS method. For monosaccharide analysis, the polysaccharide extracts/fractions were methanolyzed with 0.5 M methanolic-HCl (Supelco) at 80° C. for 16 h, re-N-acetylated with 500 μL of methanol, 10 μL of pyridine and 50 μL of acetic anhydride, and then treated with the Sylon HTP® trimethylsilylating reagent (Supelco) for 20 min at room temperature, dried and redissolved in hexane. GC-MS analysis of the trimethylsilylated derivatives was carried out using a Hewlett-Packard (HP) Gas Chromatograph 6890 connected to a HP 5973 Mass Selective Detector. Samples were dissolved in hexane prior to splitless injection into a HP-5MS fused silica capillary column (30 m×0.25 mm I.D., HP). The column head pressure was maintained at around 8.2 psi to give a constant flow rate of 1 mL/min using helium as carrier gas. Initial oven temperature was held at 60° C. for 1 min, increased to 140° C. at 25° C./min, to 140° C. at 25° C./min, and then increased to 300° C. at 10° C./min.

The carbohydrate composition analyses of crude Reishi extract, fraction 3, F3G1, F3G2 and F3G3 all indicated that glucose and mannose exist as the major components together with smaller components of other sugars including fucose, galactose, N acetylglucosamine and xylose (Table 3). It is of interest that the percentage of galactose decreased significantly in F3G2 and F3G3.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto. All references cited herein are incorporated by reference in their entirety.

TABLE 1

Carbohydrate compositions of crude Reishi extract.

| Sugar components | Percentage (%) |
|---|---|
| D-glucose | 58.0 |
| D-mannose | 15.5 |
| L-fucose | 9.7 |
| D-galactose | 9.3 |
| D-xylose | 5.4 |
| D-GlcNAc | 1.0 |
| L-Rham | 0.5 |

TABLE 2

Amino acid analysis of Reishi extract.

| Amino acid | Relative abundance | Amino acid | Relative abundance |
|---|---|---|---|
| Asp | 117 | Met | 6 |
| Thr | 66 | Ile | 36 |
| Ser | 54 | Leu | 55 |
| Glu | 120 | Tyr | 16 |
| Pro | 60 | Phe | 28 |
| Gly | 108 | His | 12 |
| Ala | 100 | Lys | 21 |
| Val | 61 | Arg | 22 |

TABLE 3

Carbohydrate compositions of fraction 3, F3G1, F3G2, and F3G3

| | Percentage (%) | | | | | |
|---|---|---|---|---|---|---|
| | L-Fucose | D-Xylose | D-Mannose | D-Galactose | D-GlcNAc | D-Glucose |
| fraction 3 | 7.1 | 3.1 | 15.1 | 13.5 | 1.20 | 58.1 |
| F3G1 | 8.0 | 5.7 | 10.2 | 12.6 | 0.25 | 63.2 |
| F3G2 | 6.2 | 4.5 | 18.3 | 5.3 | 0.78 | 64.9 |
| F3G3 | 8.4 | 7.2 | 14.5 | 2.9 | 1.18 | 65.7 |

TABLE 4

Cytokine expression of mouse splenocytes treated different Reishi samples[a]

| entry | samples | cytokine expression[b] | | | | | | | | | |
|---|---|---|---|---|---|---|---|---|---|---|---|
| | | IL-1β | IL-2 | IL-4 | IL-6 | INF-γ | IL-12 | TNF-α | GM-CSF | G-CSF | M-CSF |
| 1 | crude Reishi extract | + | − | − | ± | ± | + | + | − | + | + |
| 2 | fraction 3 | + | − | − | + | + | + | + | + | + | + |
| 3 | F3G1 | + | − | − | − | − | + | + | − | + | ± |
| 4 | F3G2 | + | − | − | + | + | + | + | + | + | + |
| 5 | F3G3 | + | − | − | − | − | ± | + | − | ± | ± |

[a]Each sample was evaluated at four concentrations including $10^2$, $10^1$, $10^0$ and $10^{-1}$ μg/mL. The cells ($3 \times 10^6$ cells/mL) were incubated at 37° C. with 5% $CO_2$.
[b]+, indicating a significant increase of cytokine expression; −, indicating no increase of cytokine expression; ±, showing an increase but not significant of cytokine mRNAs.

TABLE 5

Primer Sequences Used in RT-PCT Experiments

| Cytokine | Sequences (S: sense, A: anti-sense) | | SEQ ID NO | Annealing temp (° C.) | Size of PCR product (bp) |
|---|---|---|---|---|---|
| IL-1β | S | 5'-CAACCAACAAGTGATATTCTCCATG-3' | 1 | 55 | 152 |
| | A | 5'-GATCCACACTCTCCAGCTGCA-3' | 2 | | |
| IL-2 | S | 5'-TGATGGACCTACAGGAGCTCCTGAG-3' | 3 | 59 | 167 |
| | A | 5'-GAGTCAAATCCAGAACATGCCGCAG-3' | 4 | | |
| IL-4 | S | 5'-ACGAGGTCACAGGAGAAGGGACGCCATGCA-3' | 5 | 71 | 221 |
| | A | 5'-TCATTCATGGAGCAGCTTATCGATGAATCC-3' | 6 | | |
| IL-6 | S | 5'-GTGACAACCACGGCCTTCCCTACT-3' | 7 | 53 | 313 |
| | A | 5'-GGTAGCTATGGTACTCCA-3' | 8 | | |
| IL-12 | S | 5'-TGTTGTAGAGGTGGACTGG-3' | 9 | 67-65 | 483 |
| | A | 5'-TGGCAGGACACTGAATACTT-3' | 10 | | |
| IFN-γ | S | 5'-TGGAGGAACTGGCAAAAGGATGGT-3' | 11 | 53 | 336 |
| | A | 5'-TTGGGACAATCTCTTCCCCAC-3' | 12 | | |
| TNF-α | S | 5'-GCGACGTGGAACTGGCAGAAG-3' | 13 | 65 | 383 |
| | A | 5'-GGTACAACCCATCGGCTGGCA-3' | 14 | | |
| GM-CSF | S | 5'-TGTGGTCTACAGCCTCTCAGCAC-3' | 15 | 65 | 368 |
| | A | 5'-CAAAGGGGATATCAGTCAGAAAGGT-3' | 16 | | |
| G-CSF | S | 5'-ATCCAGGCCAGCGGCTCGG-3' | 17 | 63-65 | 467 |
| | A | 5'-GGGCTTTCTGCTCAGGTCTAG-3' | 18 | | |
| M-CSF | S | 5'-GTAGCCACATGATTGGGAATGG-3' | 19 | 67-65 | 304 |
| | A | 5'-TCATGGAAAGTTCGGACACAGG-3' | 20 | | |
| GAPDH | S | 5'-ACGACCCCTTCATTGACC-3' | 21 | 57 | 203 |
| | A | 5'-AGACACCAGTAGACTCCACG-3' | 22 | | |

Scheme 1

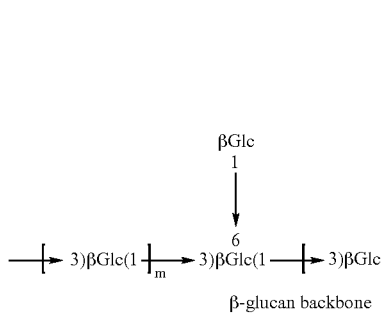

β-glucan backbone

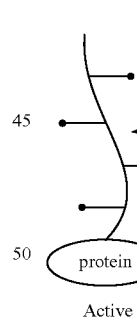

α-mannan backbone

Scheme 2

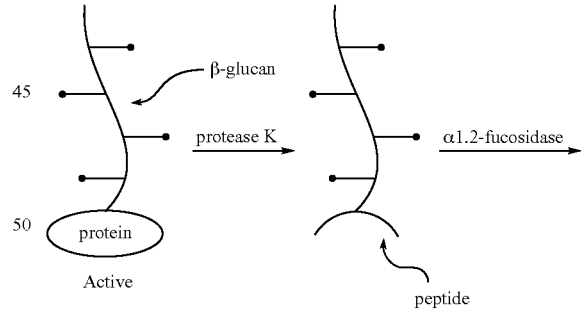

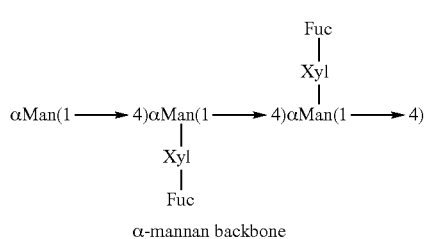

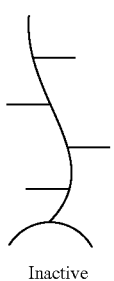

REFERENCES 1. (a) Lien, E.-J. in Progress in Drug Research, Fortschritte der Arzneimittelforschung Progress des researcges pharmaceutiques, Birkhäuser Verlaq: Basel, 1990, Vol. 34, pp 395-420. (b) Shiao, M. S.; Lee, K. R.; Lin, L. J.; Wang, C T. In *Food photochemicals for Cancer Prevention:* II. Ho, Ct.; Osawa, T.; Huang, M. T.; Rosen, R. T., Eds.; American Chemical Society: Washington D. D., 1994, pp 342-354; Furusawa, E.; Chou, S. C.; Furasawa, S.; Hirazawa, A.; Dang, Y. Phytotherapy Res. 1992, 6, 300-304; Franz, G., Planta Medica, 1989, 55, 493-497.
2. Stone, y.; Okuda, R; Wada, N.; *Agr. Biol. Chem.* 1985, 49, 2641-2653.
3. (a) Wang, S.-Y.; Hsu, M.-L.; Hsu, H. *Int. J. Cancer* 1997, 70, 699-705. (b) Vetvicka, V.; Thornton, B. P.; Ross, G. D. *J. Clin. Invst.* 1996, 98, 50-61. (c) Van Strijp, J. A. G.; Russel, D. G.; Tuomanen, E.; Brown, E. J.; Wright, S. D. *J. Immunol.* 1993, 151, 3324-3336. (d) Muller, A.; Rice, P. J.; Ensley, H. E.; Coogan, P. S.; Kalbfleisch, J. H.; Kelley, J. L.; Love, E. J.; Portera, C. A.; Ha, T.; Browder, I. W.; Williams, D. L. *J. Immunol.* 1996, 156, 3418-3425.
4. Usui, T.; Iwasaki, Y.; Mizuno, T. *Carbohydr. Res.* 1983, 115, 273-280.
5. (a) Miyazaki, T.; Nishijime, M. *Carbohydr. Res.* 1982, 109, 290-294. (b) Wang, Y. Y.; Khoo, K. K.; Chen, S. T.; Lin, C. C.; Wong, C. H.; Lin, C. H. Bioorg. Med. Chem. 2002, 10, 1057-1062.
6. (a) Somani, B. L.; Khanade, J.; Sinha, R. *Anal. Biochem.* 1987, 167, 327-330. (b) Jermyn, M: A. *Anal. Biochem.* 1975, 68, 332-335. (c) Halhoul, M. N.; Kleinberg, I. *Anal. Biochem.* 1972, 50, 337-343.
7. Mosmanni, T. *J. Immunol. Methods* 1983, 65, 55-63.
8. (a) Bowden, R.; Tate, S. M. Soto, S.; Specter, S. *Int. J. Immunopharmacol.* 1999, 21, 815-827. (b) Murphy, E.; Hieny, S.; Sher, A; O'Garra, A. *J. Immunol. Methods* 1993, 162, 211-223.
9. Spachman, D. H.; Moore, S.; Stein, W. H. *Anal. Chem.* 1958, 30, 1190-1206. For a recent example, please see: Lo, C.-H.; Chiou, S.-H. *J. Chromatogr.* 1990, 530, 129-136.
10. Sanchez J.-C.; Chiappe, D.; Converset, V.; Hoogland, C.; Binz, P.-A; Paesano, S.; Appel R. D.; Wang, S.; Sennitt, M.; Norian, A; Cawthorne, M. A.; Hochstrasser, D. F. *Proteomics* 2001, 1, 136-163.

---

What is claimed is:

1. A method for modulating an immune response in an organism in need thereof comprising administering to said organism an effective amount of a purified extract from *Ganoderma lucidum* comprising a polysaccharide or glycopeptide component having a terminal fucose residue with α1,2-fucosidic linkages, wherein said purified extract is obtained by the method comprising:

homogenizing a tissue of *Ganoderma lucidum*; extracting the homogenized tissue with aqueous alkaline solution to form a crude extract; and subjecting the crude extract to gel filtration chromatography to form one or more fractions buffered at a pH of about 7, the one or more fractions comprising said polysaccharide or glycopeptides component having terminal fucose residues with α1,2-fucosidic linkages; wherein the purified extract comprises at least one of the fractions.

2. The method of claim 1 wherein the aqueous alkaline solution is NaOH solution.

3. The method of claim 1 wherein the NaOH solution is a 0.1 N solution.

4. The method of claim 1 wherein the gel filtration chromatography step is performed using a Sephracryl S-500 column.

5. A method for modulating an immune response in an organism in need thereof comprising administering to said organism an effective amount of a purified extract from *Ganoderma lucidum* comprising a polysaccharide or glycopeptide component having a terminal fucose residue with α1,2-fucosidic linkages, wherein said purified extract is obtained by the method comprising:

homogenizing a tissue of *Ganoderma lucidum*; extracting the homogenized tissue with aqueous alkaline solution to form a crude extract; subjecting the crude extract to gel filtration chromatography to form one or more fractions buffered at a pH of about 7; and partitioning the one or more fractions with an anion exchanger to form one or more subfractions, the one or more subfractions comprising said polysaccharide or glycopeptide comprising terminal fucose residues with a 1,2-fucosidic linkages; wherein the purified extract comprises at least one of the subfractions.

6. A method for modulating an immune response in an organism in need thereof comprising administering to said organism an effective amount of a purified extract from *Ganoderma lucidum* comprising a polysaccharide or glycopeptide component having a terminal fucose residue with α1,2-fucosidic linkages, wherein said purified extract is obtained by the method comprising:

homogenizing a tissue of *Ganoderma lucidum*; extracting the homogenized tissue with aqueous alkaline solution to form a crude extract; subjecting the crude extract to gel filtration chromatography to form one or more fractions buffered at a pH of about 7; partitioning the one or more fractions with an anion exchanger to form one or more subfractions; and partitioning the one or more subfractions by gel filtration to form one or more partitioned subfractions, the one or more partitioned subfractions comprising said polysaccharide or glycopeptide comprising terminal fucose residues with α1,2-fucosidic linkages; wherein the purified extract comprises at least one of the partitioned subfractions.

7. The method of claim 1 wherein said organism is a human.

* * * * *